United States Patent
Lash et al.

(10) Patent No.: US 6,280,428 B1
(45) Date of Patent: Aug. 28, 2001

(54) ABSORBENT ARTICLE HAVING FLAPS WITH STEP CONFIGURATION AND ZONES OF EXTENSIBILITY

(75) Inventors: Glen Ray Lash, Cincinnati, OH (US); Nami Terada, Hyogo (JP); Robb Eric Olsen, Cincinnati, OH (US); Shirley Lee Chow, Cincinnati, OH (US); Jeffrey Vincent Bamber, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 09/230,201
(22) PCT Filed: Oct. 3, 1996
(86) PCT No.: PCT/US96/15957
  § 371 Date: Oct. 26, 1998
  § 102(e) Date: Oct. 26, 1998
(87) PCT Pub. No.: WO97/12577
  PCT Pub. Date: Apr. 10, 1997

Related U.S. Application Data (63) Continuation-in-part of application No. 08/539,915, filed on Oct. 6, 1995, now abandoned.

(51) Int. Cl.[7] .................................................. A61F 13/15
(52) U.S. Cl. ................... 604/385.04; 604/386; 604/387; 604/385.03; 604/385.24; 604/390
(58) Field of Search ............................. 604/385.1, 387, 604/386, 390, 399, 397, 378, 385.03, 385.04, 385.24

(56) References Cited

U.S. PATENT DOCUMENTS

| | | | |
|---|---|---|---|
| 4,900,319 | * 2/1990 | Richwine | 604/385.1 |
| 4,950,264 | * 8/1990 | Osborn, III | 604/385.1 |
| 5,009,653 | * 4/1991 | Osborn, III | 604/385.1 |
| 5,098,422 | * 3/1992 | Davis et al. | 604/385.1 |
| 5,125,918 | * 6/1992 | Seidy | 604/386 |
| 5,154,715 | * 10/1992 | Van Iten | 604/387 |
| 5,201,727 | * 4/1993 | Nakanishi et al. | 604/390 |
| 5,207,665 | * 5/1993 | Davis et al. | 604/399 |
| 5,217,448 | * 6/1993 | Glaug et al. | 604/397 |
| 5,221,275 | * 6/1993 | Van Iten | 604/387 |
| 5,248,309 | * 9/1993 | Serbiak et al. | 604/368 |
| 5,275,591 | * 1/1994 | Mavinkurve | 604/387 |
| 5,281,209 | * 1/1994 | Osborn, III et al. | 604/385.1 |
| 5,344,416 | * 9/1994 | Niihara | 604/385.1 |
| 5,354,400 | * 10/1994 | Lavash et al. | 156/227 |
| 5,374,260 | * 12/1994 | Lemay et al. | 604/378 |
| 5,383,869 | * 1/1995 | Osborn, III | 604/385.1 |
| 5,415,650 | * 5/1995 | Sigl | 604/387 |
| 5,429,630 | * 7/1995 | Beal et al. | 604/385.1 |

FOREIGN PATENT DOCUMENTS

| | | | |
|---|---|---|---|
| WO 93/06805 | * 4/1993 | (WO) | 604/385.2 |
| WO 94/14398 | 7/1994 | (WO) | . |
| WO 95/07675 | 3/1995 | (WO) | . |
| WO 95/08311 | * 3/1995 | (WO) | 604/385.2 |

* cited by examiner

*Primary Examiner*—John G. Weiss
*Assistant Examiner*—Michael Bogart
(74) *Attorney, Agent, or Firm*—Matthew P. Fitzpatrick; Jeffrey V. Bamber (57) ABSTRACT

Absorbent articles such as sanitary napkins, panty liners, adult incontinence devices, and the like, which have flaps are disclosed. The absorbent articles have flaps with a step configuration. The absorbent articles may also have a deformed hinge that is located between at least a portion of the main body portion of the absorbent article and the flaps, and zones of extensibility for relieving the stresses that develop in the flaps when the flaps are folded down and under a wearer's undergarment.

1 Claim, 6 Drawing Sheets

ABSORBENT ARTICLE HAVING FLAPS WITH STEP CONFIGURATION AND ZONES OF EXTENSIBILITY

CROSS REFERENCE

This application is a continuation in part of U.S. application Ser. No. 08/539,915 filed Oct. 6, 1995, now abandoned.

FIELD OF THE INVENTION

The present invention relates to absorbent articles such as sanitary napkins, panty liners, adult incontinence devices, and the like. Still more particularly, the present invention concerns absorbent articles such as sanitary napkins, and the like having flaps with a step configuration. The absorbent articles are preferably also provided with a deformed hinge and zones of extensibility for relieving the stresses that develop in the flaps when the flaps are folded down and under a wearer's undergarment.

BACKGROUND OF THE INVENTION

Absorbent articles, particularly sanitary napkins, having wings or flaps are disclosed in the patent literature and are available in the marketplace. Sanitary napkins having flaps of the various types are disclosed in U.S. Pat. No. 4,687,478, entitled "Shaped Sanitary Napkin With Flaps", which issued to Van Tilburg on Aug. 18, 1987, U.S. Pat. No. 4,608,047, entitled "Sanitary Napkin Attachment Means", which issued to Mattingly on Aug. 26, 1986, U.S. Patent No. B1 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697. entitled "Disposable Sanitary Shield For Undergarments", which issued to Rickard on Aug. 20, 1968, U.S. Pat. No. 2,787,271, entitled "Sanitary Napkin", which issued to Clark on Apr. 2, 1957; and design patent Des. 365,147 issued to Hamel on Dec. 12, 1995.

A number of variations on the types of flaps described above have been presented in an attempt to solve various problems. U.S. Pat. No. 4,900,320 issued to McCoy on Feb. 13, 1990, discloses a sanitary napkin having flaps affixed at points inward from the longitudinal edge of the napkin. U.S. Pat. No. 4,911,701 issued to Mavinkurve on Mar. 27, 1990, discloses a sanitary napkin having elastic means for providing greater convex shape to the body-facing portion of the central absorbent and for enabling adhesive-free placement of the flaps of the napkin. U.S. Pat. No. 4,940,462 issued to Salerno on July 10, 1990, discloses a sanitary napkin with longitudinally expandable flaps. A sanitary napkin having flaps with stress relief means in the form of a notch or a slit is described in U.S. Pat. No. 4,917,697 which issued to Osborn, III, et al. on Apr. 17, 1990. U.S. Pat. No. 5,389,094 issued to Lavash et al. on Feb. 14, 1995, discloses sanitary napkins (and other types of absorbent articles) having flaps and zones of differential extensibility.

Although the sanitary napkins described in the Lavash, et al. patent work quite well, the search for sanitary napkins that have improved flaps has continued. For example, when flaps are wrapped around the curved side edges of the crotch of a wearer's undergarment, stresses are exerted on the flap fasteners, particularly with longer flaps. These stresses tend to cause the flap fasteners to become unattached from the surface to which they are attached, whether it be the underside of the wearer's panties or the opposing flap. This is referred to herein as "wing pop-off". In addition, there is a tendency for the portions of the flaps located in the region of the juncture of the flaps with the main body portion of the sanitary napkin, particularly at those portions of the flaps that are spaced farthest away from the transverse centerline of the flaps (that is, the end portions of the flaps), to wrinkle and be compressed inward due to the forces exerted thereon by the wearer's panty elastics and the wearer's legs.

It is, therefore, an object of the present invention to provide an absorbent article having flaps, such as a sanitary napkin, with a structure that allows the flaps to cover as large an area of the wearer's panties as possible without the fasteners thereon becoming unattached.

It is another object of the present invention to provide an absorbent article having flaps, such as a sanitary napkin, with a structure that resists the tendency for the end portions of the flaps to wrinkle and be compressed inward.

These and other objects of the present invention will be more readily apparent when considered in reference to the following description and when taken in conjunction with the accompanying drawings.

SUMMARY OF THE INVENTION

In accordance with the present invention, an absorbent article, such as a sanitary napkin, is provided. The sanitary napkin has flaps with a step configuration and preferably also has a deformed hinge and zones of extensibility for relieving the stresses that develop in the flaps when the flaps are folded around and under the edges of the crotch of the wearer's panties.

The sanitary napkin has a principal longitudinal centerline and a principal transverse centerline. The sanitary napkin comprises a main body portion and a pair of flaps joined to the main body portion. The main body portion of the sanitary napkin comprises a liquid pervious topsheet, a liquid impervious backsheet joined to the topsheet, an absorbent core positioned between the topsheet and the backsheet. The main body portion has two spaced apart longitudinal edges and two spaced apart transverse end edges.

The flaps are each joined to the main body portion at a juncture. The flaps extend laterally outward from at least the central region of the main body portion beyond the longitudinal side edges of the main body portion. In one preferred embodiment, the flaps are integral extensions of the topsheet and backsheet. The flaps are divided into a front half and a back half by a flap transverse centerline. The flaps each have two corner regions which are located adjacent to the area of the ends of the junctures of the flaps with the main body portion. One corner region is located adjacent the area of the juncture in each direction spaced away from the principal transverse centerline.

The flaps have a step configuration in which a portion of the flaps adjacent to the juncture is longer as measured in the longitudinal direction than a portion of the flaps located adjacent to the distal edges of the flaps. The step configuration provides the flaps with improved protection against staining of the sides of the wearer's undergarments (or "side soiling protection"), while reducing the tendency for the flap fasteners to become unattached from the undergarment (reducing "wing pop-off"). The sanitary napkin preferably further comprises a deformed hinge (or bending zone) located in a region that includes the juncture of the flaps with the main body portion and zones of differential extensibility in the corner regions of the flaps. The deformed hinge provides at least one axis about which the flaps may fold relative to the main body portion. The zones of differential extensibility allow the corner regions to extend outward (preferably in a generally transverse direction) to provide a means for the relief of the stresses that develop in the flaps of the sanitary napkin when the flaps are folded down and under the curved side edges of the wearer's undergarments.

In a preferred embodiment, at least a portion of the deformed hinge comprises a portion of the sanitary napkin that has a strainable network formed therein. The strainable network comprises at least two visually distinct regions, referred to as a first region and a second region. The network is configured so that at least one of the regions, the second region, has a surface-pathlength (dimension measured along the surface) which is greater than that of the first region. The second region exhibiting the longer surface-pathlength preferably comprises one or more rib-like elements. The first region with the shorter surface-pathlength is preferably substantially planar. In this embodiment, the portion of the deformed hinge comprising this type of strainable network is preferably located at least in the region of the flap transverse centerline.

DETAILED DESCRIPTION OF THE INVENTION

The present invention relates to absorbent articles that are worn in an undergarment, such as sanitary napkins, panty liners, incontinence devices, and the like. More particularly, the present invention relates to absorbent articles having flaps with a step configuration for improved protection of the wearer's undergarment. The sanitary napkin preferably also has a deformed hinge and zones of extensibility for relieving the stresses that develop in the flaps when they are folded down and under a wearer's undergarment.

Figure 1:
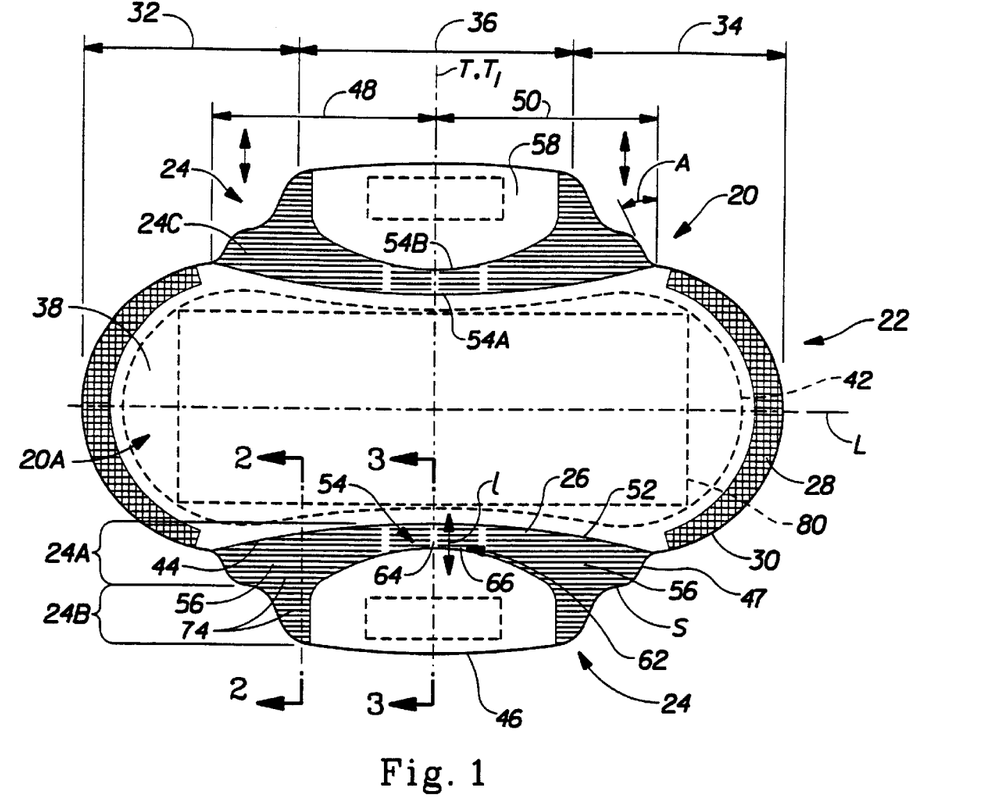
FIG. 1 is a top plan view of a preferred sanitary napkin embodiment of the present invention.

A preferred embodiment of a sanitary napkin 20 of the present invention is shown in FIG. 1. As shown in FIG. 1, the sanitary napkin 20 basically comprises an absorbent means (or "main body portion") 22, and two flaps 24. The sanitary napkin 20 has two surfaces, a body-contacting surface or "body surface" 20A and a garment surface 20B. The sanitary napkin 20 is shown in FIG. 1 as viewed from its body surface 20A. The body surface 20A is intended to be worn adjacent to the wearer's body. The garment surface 20B is intended to be placed adjacent to the wearer's undergarments when the sanitary napkin 20 is worn.

The sanitary napkin 20 has two centerlines, a principal longitudinal centerline L and a principal transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

FIG. 1 shows that the main body portion 22 of the sanitary napkin 20 comprises the portion of the sanitary napkin without the flaps 24. The main body portion 22 has two spaced apart longitudinal edges 26, two spaced apart transverse or end edges (or "ends") 28, which together form the periphery 30 of the main body portion. The main body portion 22 also has two end regions, which are designated first end region 32 and second end region 34. A central region 36 is disposed between the end regions 32 and 34. The end regions 32 and 34 extend outwardly in the longitudinal direction from the edges of the central region 36 about ⅛ to about ⅓ of the length of the main body portion. A detailed description of the characteristics of a central region and two end regions for a sanitary napkin is contained in U.S. Pat. No. 4,690,680 issued to Higgins on Sep. 1, 1987.

The main body portion 22 of the sanitary napkin 20 can be of any thickness, including relatively thick, intermediate thickness, relatively thin, or even very thin (or "ultra thin"). An "ultra-thin" sanitary napkin 20 as described in U.S. Pat. Nos. 4,950,264 and 5,009,653 issued to Osborn preferably has a caliper of less than about 3 millimeters. The embodiment of the sanitary napkin 20 shown in FIGS. 1–3 of the drawings is intended to be an example of a sanitary napkin of an intermediate thickness. The main body portion 22 of the sanitary napkin 20 may also be relatively flexible, so that it is comfortable for the wearer. It should be understood that the sanitary napkin shown is merely one embodiment, and that the present invention is not limited to absorbent articles of the type or having the specific configurations shown in the drawings.

Figure 2:
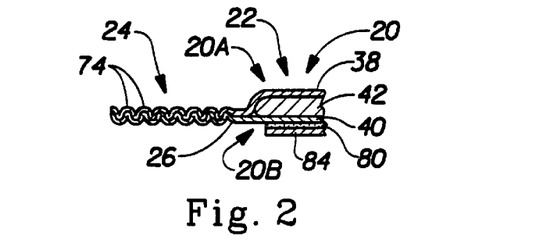
FIG. 2 is a lateral cross-sectional view taken along line 2—2 of FIG. 1 through the corner region of one of the flaps of the sanitary napkin.

FIG. 2 shows the individual components of the main body portion 22 of the sanitary napkin 20 of the present invention. The main body portion 22 of the sanitary napkin preferably comprises at least three primary components. These include a liquid pervious topsheet 38, a liquid impervious backsheet 40, and an absorbent core 42 positioned between the topsheet 38 and the backsheet 40. The topsheet, the backsheet, and the absorbent core may be assembled in a variety of configurations known in the art (including layered or "sandwich" configurations and wrapped or "tube" configurations).

Suitable materials for the components of the main body portion 22, and some of the various configurations in which such components can be assembled are described generally in U.S. Pat. No. 4,321,924, "Bordered Disposable Absorbent Article" issued to Ahr on Mar. 30, 1982; U.S. Pat. No. 4,425,130, "Compound Sanitary Napkin" issued to DesMarais on Jan. 10, 1984; U.S. Pat. No. 4,950,264, "Thin, Flexible Sanitary Napkin" issued to Osborn on Aug. 21, 1990; U.S. Pat. No. 5,308,346, "Elasticized Sanitary Napkin" issued to Sneller, et al. on May 3, 1994; U.S. Pat. No. 5,389,094 "Absorbent Article Having Flaps and Zones of Differential Extensibility" issued to Lavash, et al. on Feb. 14, 1995; and U.S. Pat. No. 5,558,663, "Absorbent Article Having Undergarment Covering Components With Zones of Extensibility" issued to Weinberger, et al. on Sep. 24, 1996. The main body portion 22 of the sanitary napkin may also be comprised of one or more extensible components such as those sanitary napkins, and the like described in U.S. patent application Ser. No. 07/915,133 filed Jul. 23, 1992, in the name of Osborn, et al. (PCT Publication No. WO 93/01785, published Feb. 4, 1993), now pending in the form of allowed continuation application Ser. No. 08/503,895, filed on Jul. 18, 1995; and U.S. patent application Ser. No. 07/915,284 filed Jul. 23, 1992, in the name of Osborn, et al. (PCT Publication No. 93/01786, published Feb. 4, 1993), now pending in the form of allowed divisional application Ser. Nos. 08/472,156 and 08/476,238, filed on Jun. 7, 1995.

Figure 3:
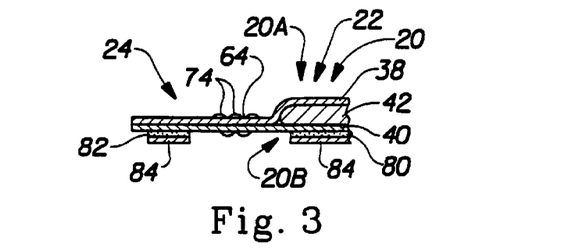
FIG. 3 is a lateral cross-sectional view taken along line 3—3 of FIG. 1 through the center portion of one of the flaps.

FIGS. 1–3 show a preferred embodiment of the sanitary napkin 20 assembled in a sandwich construction in which the topsheet 38 and the backsheet 40 have length and width dimensions generally larger than those of the absorbent core 42. The topsheet 38 and the backsheet 40 extend beyond the edges of the absorbent core 42 to form portions of the periphery 30. The topsheet 38 is preferably joined to the body-facing side of the absorbent core 42 and the backsheet 40 is preferably joined to the garment-facing side of the absorbent core. The topsheet 38 and backsheet 40 can be joined to the absorbent core in any suitable manner known in the art for this purpose, such as by an open pattern of adhesives. The portions of the topsheet 38 and backsheet 40 that extend beyond the edges of the absorbent core are preferably also joined to each other. These portions of the topsheet 38 and backsheet 40 can be joined in any suitable manner known in the art for this purpose. Preferably, in the embodiment shown, these portions of the topsheet 38 and backsheet 40 are joined using adhesives over substantially the entire portions that extend beyond the edges of the absorbent core 42, and a crimp seal at the end edges 28 of the main body portion where the topsheet 38 and backsheet 40 are densified by the application of pressure or heat and pressure.

The sanitary napkin 20 shown in FIGS. 1–3, as discussed above, also comprises a pair of flaps 24 that are joined to the main body portion 22. The flaps 24 extend laterally outward beyond the longitudinal side edges 22 of the main body portion 22 from their proximal edges 44 to their distal edges (or "free ends") 46. The flaps 24 extend outward from at least the central region 36 of the main body portion 22. As shown in FIG. 1, each flap 24 is divided into a front half 48, and a back half 50 by a flap transverse centerline $T_1$. The flap transverse centerline $T_1$ may coincide with the principal transverse centerline T of the sanitary napkin, but this is not absolutely required.

The flaps 24 can be joined to the main body portion 22 in any suitable manner. The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. Preferably, in the embodiment shown in FIGS. 1–3, the flaps 24 are integral with the main body portion 22 (that is, the flaps 24 comprise integral extensions of the topsheet 38 and backsheet 40). The extension of the topsheet 38 and backsheet 40 may be joined together by adhesives over their entire interface to form the flaps 24.

In an alternative embodiment, however, a portion of the topsheet 38 and backsheet 40 that are joined together to form the flaps 24 may be substantially free of adhesive between the same to leave a "glue-free window" in a portion of the flaps 24. The topsheet 38 and backsheet 40 are, however, preferably bonded to each other at least along the entire perimeter of the flaps 24 and in the extensible portions of the flaps 24. Thus, the flaps 24 may have a "glue-free window" in all or a portion of the region designated 58. In embodiments, such as that shown in FIG. 13, that are not provided with a deformed hinge, the glue-free window can extend inward all the way to the longitudinal side edges of the absorbent core 42. In a preferred embodiment, the glue free window is a rectangular area measuring about 68 mm by about 25 mm that is located in the same region of the flaps 24 as the flap adhesive 82. The glue-free window can be used to provide this portion of the flaps 24 with greater flexibility since portions of the flaps comprising an unbonded topsheet and backsheet are free to bend independently of each other and will not be as stiff as portions of the topsheet and backsheet that are adhesively laminated together. The glue-free window may, thus, make the flaps 24 more comfortable for the wearer.

In other alternative embodiments, the flaps 24 can comprise one or more separate components that are joined to the main body portion 22. Preferably, in such a case, the flaps 24 each comprise a separate component that is joined to the garment-facing side of the main body portion 22. The flaps 24 can be joined to the main body portion 22 at, or inward of the longitudinal side edges 26 of the main body portion 22. In such alternative embodiments, the flaps 24 are preferably otherwise unattached to the garment-facing side of the main body portion 22 of the sanitary napkin 20 between the points where they are attached to the main body portion and the longitudinal side edges 26 of the main body portion. The flaps 24 in these latter embodiments can be joined to the garment-facing side of the main body portion 22 by any suitable attachment mechanism. Suitable attachment mechanisms include, but are not limited to adhesives, and the like.

The flaps 24 are each joined to (or associated with) main body portion 22 along a juncture. This is typically a longitudinally-oriented (or "longitudinal") juncture, such as lines of juncture 52. As used herein, the terms "juncture" (or "line of juncture") refer to regions where the flaps 24 extend from or are joined to the main body portion 22. These regions can be any of various curved or straight lines, but they are not limited to lines. Thus, these regions can comprise flanges, strips, intermittent lines, and the like. The line of juncture 52 in the embodiment illustrated in FIG. 1 can be considered to be defined by concave inwardly-oriented regions or lines if the proximal edges 44 of the flaps 24 are considered to coincide with the inwardmost boundary of the hinge 54 described herein.

The flaps 24 have a step configuration in which a portion of the flaps 24 adjacent to the juncture 52 is longer as measured in the longitudinal direction than the portion of the flaps located adjacent to the distal edges of the flaps. The flaps 24 comprise a proximal portion (or panty protective portion) 24A and a distal portion (or flap securement portion) 24B. The proximal portion 24A is the portion of the flaps 24 located adjacent to the juncture 52 that provides protection against staining of the wearer's undergarments. The distal portion 24B is the portion of the flaps 24 located adjacent to the distal edges 46 of the flaps 24. The distal portion 24B, in addition to providing protection against staining of the wearer's undergarments, contains a fastener for securing the flaps 24 around the sides of the wearer's undergarment.

The term "step configuration", as used herein, means that there is a discontinuity in the configuration of the outer edge or periphery 47 of the flaps 24 at the ends of the flaps 24. More specifically, the discontinuity in the periphery of the flaps 24 is located between the proximal portion 24A and the distal portion 24B of the flaps 24. In the preferred embodiment shown in FIG. 1, the flaps 24 have a step configuration in which the outer edge 47 of the flaps 24 initially extends laterally outward from the main body portion 22 at an angle, A. This angle, A, is oriented inward toward the flap transverse centerline $T_1$ relative to a line drawn in the transverse direction through the proximal edge of the flap. At the interface between the proximal portion 24A and the distal portion 24B, the outer edge 47 of the flaps 24 turns inward so that it forms a greater angle toward the flap transverse centerline. In this area, the outer edges 47 of the flaps are nearly perpendicular to the flap transverse centerline $T_1$. Following this transition area that comprises the step, S, the outer edge 47 of the flaps returns to follow the same general angle that it made along the proximal portion 24A of the flaps 24.

The flaps 24, and the various portions thereof, can be of any suitable size (subject to the following requirement) and of many possible step configurations. The overall size of the flaps 24 can be of any size specified for flaps in the patent publications incorporated by reference herein. However, the flaps 24 should be capable of providing a soiling protection benefit. The length of the flaps 24 in the longitudinal direction should be greater than about 35 mm when measured at a distance 25 mm laterally outward from the edge of the absorbent core 42 along the flap transverse centerline $T_1$. The width or span of the flaps 24 can range from less than or equal to about one-half the width of the main body portion to greater than about one-half the width of the main body portion.

In a preferred embodiment, the proximal portion 24A of the flaps 24 is between about 100 to about 170 mm in length, and preferably is between about 120 mm to about 150 mm in length. The length of the distal portion 24B of the flaps 24 as measured in the longitudinal direction is preferably between about 50% to about 80%, more preferably about 75% of the length of the proximal portion 24A of the flaps 24. In this preferred embodiment, the width of the proximal portion 24A of the flaps 24 as measured in the transverse direction is preferably between about 20 mm to about 25 mm from the laterally outwardmost portion of the absorbent core 42 to the step (designated "S") in the flaps 24. In this embodiment, the width of the distal portion 24B of the flaps 24 as measured in the transverse direction is preferably between about 15 mm to about 30 mm from the step, S, to the laterally outwardmost portion on the distal edge 46 of the flaps 24.

Figure 11:
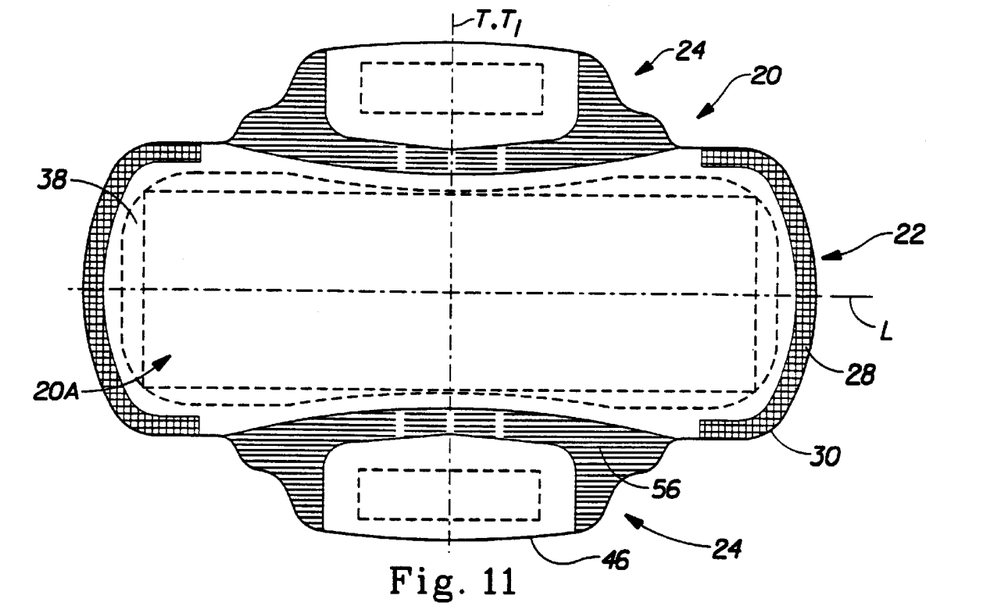
FIG. 11 is a plan view of a sanitary napkin according to the present invention that has an alternative configuration.

The step configuration provides the flaps 24 with improved protection against staining of the sides of the wearer's undergarments (or "side soiling protection"), and reduces the tendency for the flap fasteners 82 to become unattached from the undergarment (reducing "wing pop-off"). More specifically, for an ultra-thin version of this embodiment (such as is shown in FIG. 11), side soiling protection is increased by approximately 50 percent over that provided by sanitary napkins having flaps without the step configuration described herein that are currently marketed by The Procter & Gamble Company as ALWAYS ULTRA with Wings sanitary napkins. Without wishing to be bound by any particular theory, this is believed to be due to at least two main factors. The first factor is that the additional material 24C in the proximal portions 24A of the flaps 24 provides increased coverage of the sides of the wearer's undergarments. The second factor is that this additional material 24C maintains a degree (or a line) of tension between the longitudinal edges 26 of the main body portion 22 and the distal edges 46 of the flaps 24 that prevents the flap material from being compressed inward during wear. In this same embodiment, pop-off of the flaps 24 is reduced between about 25% and about 50% in comparison to flaps on the currently marketed product. Without wishing to be bound by any particular theory, the reduction in "pop-off" is believed to be due to the presence of the zones of extensibility and the fact that the distal portion 24B of the flaps that contains the flap adhesive 82 (described below) is shorter in length than the proximal portions 24A of the flaps 24, and is, therefore, under less lateral stress during wear.

Numerous alternative step shape flap embodiments are possible. For example, it is also possible for the main body portion 22 to be asymmetrical and the flaps to be offset forward or rearward of the transverse centerline T of the sanitary napkin so that the flap transverse centerline $T_1$ does not coincide with the principal transverse centerline of the sanitary napkin 20. In addition, it is possible for the relevant angles, curves, and step length to be altered from those shown in FIG. 1. Further, the relevant angles, curves, and step length can be different in the front half 48 of the flaps 24 than it is in the back half 50 of the flaps 24. For example, the length of the step (measured in the longitudinal direction) may be longer in the back half 50 of the flap 24 than in the front half 48, or vice versa. Numerous other embodiments are possible.

The sanitary napkin 20 shown in FIGS. 1–3 preferably also has a deformed region that forms a hinge 54 between the main body portion 22 and at least a portion of the flaps 24. In addition, the sanitary napkin 20 preferably has at least one zone of extensibility (or "zone of differential extensibility") 56 for relieving the stresses on the flaps 24 when they are folded around a panty crotch. These features are each described in greater detail below.

In the sanitary napkin shown in FIGS. 1–3, the hinge 54 comprises a generally longitudinally-oriented, mechanically-deformed region. As used herein, the term "deformed region" preferably refers to a generally planar unfolded web that has a three dimensional geometry created therein by the application of mechanical force to the web, typically by the application of a force having a component perpendicular to the plane of the undeformed web so that the force causes portions of the web to be displaced relative to the original plane of the web.

The hinge 54 provides a region of the sanitary napkin 20 with increased flexibility to create preferred bending axes for the flaps 24 to bend or fold about. The hinge 54 is preferably located in a region along the juncture 52 of the flaps 24 with the main body portion 22. The hinge 54, however, does not have to coincide exactly with the juncture 52 of the flaps 24 with the main body portion 22. The hinge 54 can be located laterally inboard of the juncture 52 of the flaps with the main body portion 22, on the juncture 52, laterally outboard of the juncture 52, or any combination of the foregoing. If the hinge 54 is located laterally inboard of the juncture 52 or on the juncture, the hinge 54 may be considered to be formed in at least part of the main body portion 22 (and, in the latter case, also in part of the flaps 24).

The hinge 54 can extend along the entire juncture 52 of the flaps with the main body portion 22, or along only a portion thereof. If the hinge 54 is only provided along a portion of the juncture 52, it is preferably provided in the region of the sanitary napkin 20 surrounding and including the flap transverse centerline $T_1$. The hinge 54 can be in many possible configurations. The hinge 54 can comprise a continuous region, or a plurality of spaced apart intermittent regions. The hinge 54 can be rectilinear, curvilinear, or it can comprise portions that are rectilinear and portions that are curvilinear. The hinge 54 has a laterally inwardmost, or proximal, boundary 54A and an outermost, or distal, boundary 54B. In the embodiment shown in FIGS. 1–3, at least the inwardmost boundary 54A of the hinge 54 is preferably concave inwardly relative to the distal edge 46 of the flaps 54.

The hinge 54 can be formed in any suitable manner that provides the desired region of the sanitary napkin with increased flexibility. Preferably, the hinge 54 is formed by mechanically deforming the desired regions of the sanitary napkin. It has been found that many processes suitable for providing regions of the sanitary napkin with extensibility are particularly suitable for providing regions of the sanitary napkin 20 selected for the hinge 54 with enhanced flexibility.

The hinge 54 can, for instance, be formed by a process in which the desired portions of the sanitary napkin are fed between corrugated intermeshing rolls, which has been described as pre-corrugating (or "ring rolling"). Suitable methods for ring rolling are described in U.S. Pat. No. 4,107,364 issued to Sisson on Aug. 15, 1978, U.S. Pat. No. 4,834,741 issued to Sabee on May 30, 1989, U.S. Pat. No. 5,143,679 issued to Gerald M. Weber, et al. on Sep. 1, 1992, U.S. Pat. No. 5,156,793 issued to Kenneth B. Buell, et al. on Oct. 20, 1992, and U.S. Pat. No. 5,167,897 issued to Gerald M. Weber, et al. on Dec. 1, 1992.

Alternatively, as shown in FIG. 1 for purposes of illustration, the hinge 54 is provided by forming a strainable network in the region along the juncture 52 of the flaps 24 with the main body portion 22. The process for forming a strainable network region, and structures formed thereby are described in greater detail below in conjunction with FIGS. 7–10. This technology is further described in U.S. Pat. No. 5,518,801, "Web Materials Exhibiting Elastic-Like Behavior" issued to Chappell, et al. on May 21, 1996 (PCT Publication No. WO 95/03765, published Feb. 9, 1995).

These structures (ring rolled structures and materials with strainable network regions formed therein) are especially preferred for the hinge 54 because the alternating ridges and valleys can form a plurality of flexible bending axes for the flaps 24. These types of structures also provide the hinge 54 with a degree of extensibility. The extensibility allows the portions of the flaps 24 in the hinge region 54 to expand slightly in the transverse direction to better fold around the curved sides of the wearer's panty crotch. Providing the hinge 54 by forming strainable network regions in the sanitary napkin may also be preferred when it is desired to provide the formed regions with slightly more integrity so the flaps 24 will be less likely to droop excessively at the hinge 54 because the unformed first regions or less extensible bands 64 (described below) of the strainable network will serve like "beams" that tend to provide the flaps 24 with slightly more structural rigidity and better appearance.

The process of forming a strainable network is preferred for providing the sanitary napkin 20 with a hinge 54 because (like ring rolling) such an operation can be readily adapted for use in high speed manufacturing operations. Further, the process of forming a strainable network in a material is highly preferred because it can be adapted to produce a virtually unlimited number of patterns to tailor the configuration and characteristics of the hinge 54 and zones of extensibility 56.

Typically, the base material into which the strainable network is formed comprises a single layer of material or a laminate of several layers of materials, at least one of which is a film. Preferably, in the embodiment shown in FIGS. 1–3, the material that has the strainable network formed therein comprises a laminate formed by an extension of the topsheet 38 and backsheet 40 of the sanitary napkin. The topsheet 38 preferably comprises an apertured formed film made in accordance with U.S. Pat. Nos. 4,342,314, Radel, et al. and 4,463,045, Ahr, et al. which is marketed on sanitary napkins as DRI-WEAVE topsheet material by The Procter & Gamble Company. The backsheet 40 preferably comprises a polyethylene film. The two components are preferably laminated together by adhesives.

Figure 7:
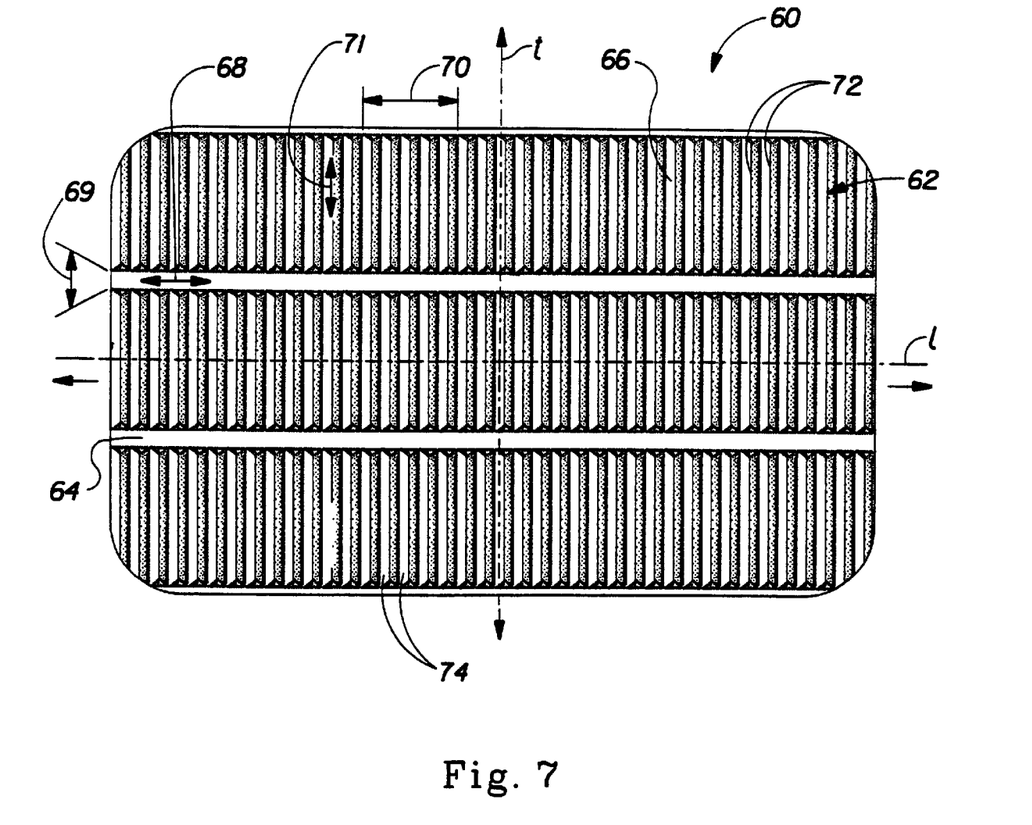
FIG. 7 is a top plan view of a web material having a strainable network of the type used in the deformed hinge of the sanitary napkin shown in FIGS. 1–3, the web material being shown in a substantially untensioned condition.
Figure 8:
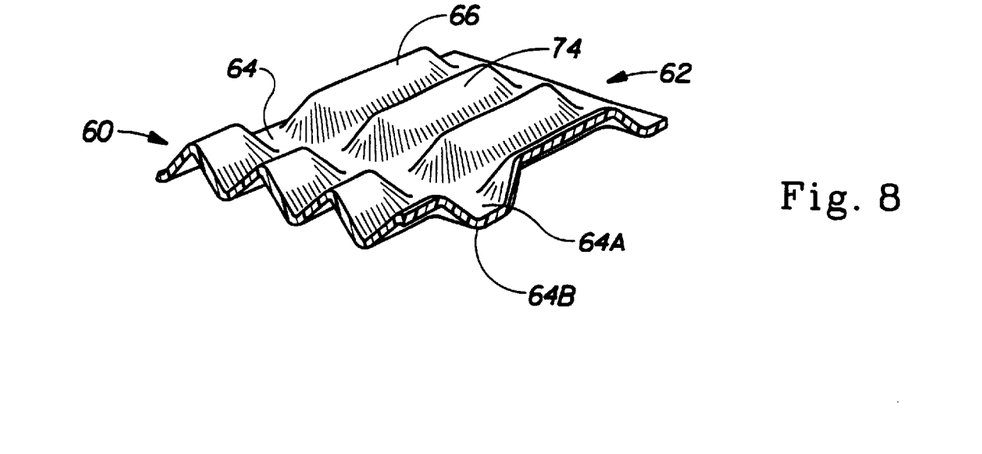
FIG. 8 is an enlarged segmented perspective illustration of the web material shown in FIG. 7 in which the web material is in a substantially untensioned condition.

The characteristics of the strainable network 62 in the hinge 54 of the sanitary napkin shown in FIGS. 1–3 will be discussed with reference to FIGS. 7–10. FIGS. 7–10 are enlarged views of a simplified version of a web material 60 having a strainable network 62 formed therein. The term "strainable network", as used herein, refers to an interconnected and interrelated group of regions which are able to be extended to some useful degree in a predetermined direction. FIGS. 7 and 8 show the web material 60 in an untensioned condition. The strainable network 62 comprises at least two distinct and dissimilar regions which are designated as first region 64 and second region 66.

In the simplified embodiment shown in FIGS. 7 and 8, the web material 60 includes a plurality of first regions 64 and a plurality of second regions 66. As shown in FIGS. 7 and 8, the first regions 64 are substantially planar regions. That is, the material within the first region 64 is in substantially the same condition before and after the formation step undergone by web material 60. The second regions 66 include a plurality of continuous, interconnected, rib-like deformations 74 which extend alternately beyond the plane of both the first and second surfaces (64A and 64B, respectively) of the first region 64. In other embodiments, the deformations 74 may extend beyond the plane of only one of the first 64A or the second 64B surfaces of the first region 64.

FIG. 7 shows that the web material 60 having the strainable network 62 formed therein has a longitudinal centerline (or axis), 1, and a lateral centerline (or axis), t. In the sanitary napkin embodiment shown in FIG. 1, the longitudinal centerline, 1, of the strainable network 62 is shown as being rectilinear and generally oriented in the transverse direction. However, the longitudinal centerline, 1, is not limited to such a configuration and orientation. The longitudinal centerline, 1, can be rectilinear, curvilinear, or partially rectilinear and partially curvilinear. The longitudinal centerline, 1, of the strainable network 62 can also be oriented in other directions, if desired.

FIG. 7 shows that the first regions 64 of the strainable network 62 have a first axis 68 and a second axis 69, wherein the first axis 68 is preferably longer than the second axis 69. In the simplified embodiment shown, the first axis 68 of the first region 64 is substantially parallel to the longitudinal axis, 1, of the web material 60 while the second axis 69 is substantially parallel to the transverse axis, t, of the web material 60. The second regions 66 of the strainable network 62 also have a first axis 70 and a second axis 71. The first axis 70 of the second region 66 is substantially parallel to the longitudinal axis 1 of the web material 60, while the second axis 71 is substantially parallel to the transverse axis t of the web material 60. In the version of the web material shown in FIGS. 7 and 8, the first regions 64 and the second regions 66 are substantially linear, extending continuously in a direction substantially parallel to the longitudinal axis 1 of the strainable web material. In other embodiments, the first regions 64, the second regions 66, or both, can be curvilinear, or partially rectilinear and partially curvilinear.

Figure 9:
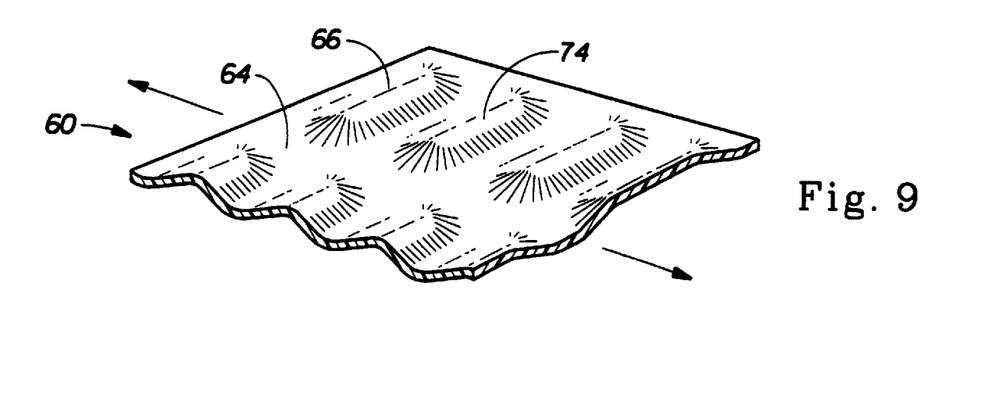
FIG. 9 is an enlarged segmented perspective illustration of the web material shown in FIG. 7 in which the web material is subjected to tension in an amount which is sufficient for a substantial portion of the deformations of the web material to enter the plane of applied elongation.
Figure 10:
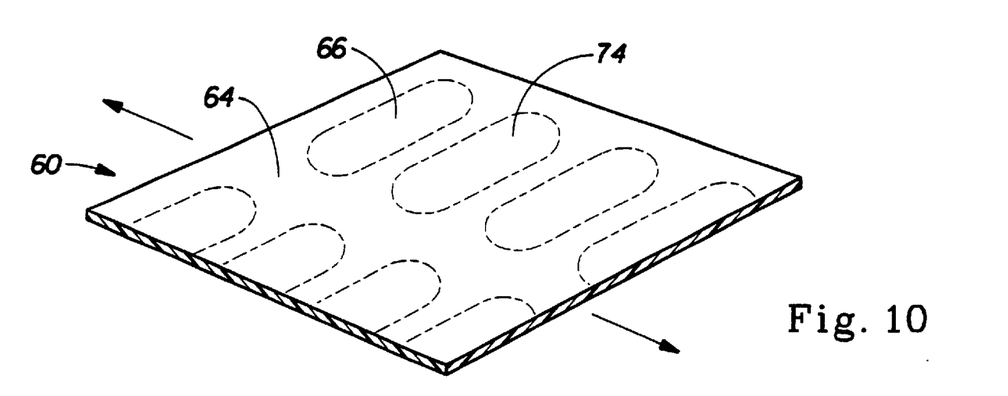
FIG. 10 is an enlarged segmented perspective illustration of the web material shown in FIG. 7 in which the web material is in a condition in which it will exhibit a second stage of resistive forces to elongation.

While the enhanced flexibility of the strainable network is of primary interest in forming the hinge 54, the strainable network also provides portions of the flaps 24 with a degree of extensibility. FIGS. 8–10 show the manner in which the web material 60 with a strainable network 62 formed therein may exhibit at least two significantly different stages of controlled resistive force to elongation when subjected to an applied elongation in a direction parallel to a predetermined axis. The strainable network 62 exhibits first resistive forces to the applied elongation (which develop between the stage shown in FIG. 8 and the stage shown in FIG. 9). The first resistive forces occur until the elongation of the web is sufficient to cause a substantial portion of the second regions 66 to enter the plane of applied elongation, as shown in FIG. 9. After the web material 60 reaches the stage shown in FIG. 9, it exhibits second resistive forces to further elongation (as illustrated by FIG. 10). Typically, when used in regions of the sanitary napkin 20 described herein, the web material will be within the first stage of resistance to elongation so the various portions of the strainable network 62 will only extend to the stage shown in FIG. 9 and adjust so as to relax back to the stage shown in FIG. 8.

The hinge 54 is created by forming the strainable network 62 into the desired portion of the sanitary napkin 20. As used herein, the term "forming" refers to the creation of a desired structure or geometry upon a web material or laminate that will substantially retain the desired structure or geometry when it is not subjected to any externally applied elongations or forces. Suitable methods for forming a strainable network into a web material include, but are not limited to embossing by mating plates or rolls, thermoforming, high pressure hydraulic forming, and casting.

The portion of the sanitary napkin 20 into which the strainable network 62 is formed can comprise a base material (or laminate) that has a relatively low extensibility under the forces that the sanitary napkin is normally subjected to when worn. When the strainable network 62 is formed therein, however, the base material can be made extensible under pre-selected forces such as those that the sanitary napkin is normally subjected to when worn.

The depth and number of deformations 74 in the strainable network 62 can be varied to control the applied force or elongation required to extend the material in the hinge regions 54 of the sanitary napkin 20. In one embodiment, the deformations 74 may be formed by two rigid plates having a pattern of meshing teeth. The outer dimensions of the pattern of teeth covers a surface area of the plates that is about 7.9" by 1.6" (20 cm by 4 cm) for each flap. On one surface of each plate are a series of teeth which are substantially triangular in cross section and taper to a radiused vertex. The teeth in this embodiment preferably have a height of 3.175 mm, and are evenly spaced with the centerlines of the teeth spaced apart at 0.075" (1.9 mm) increments. On the "toothed" side of one plate, a series of grooves (preferably three grooves to construct the embodiment shown in FIG. 1) are cut which are parallel to each other and perpendicular to the evenly spaced teeth. These grooves correspond to the undeformed regions of the base material.

The preferred base material is placed between the plates in a hydraulic press having platens larger than the plates to evenly distribute pressure. The plates are compressed so that the teeth only partially engage (or mesh). Preferably, the plates are moved so that the teeth on the opposite plates are pressed toward each other about 80 % of the distance toward full engagement (the point where the teeth would otherwise touch). Typically, in order to do this, when the base material comprises a laminate of apertured formed film and polyethylene backsheet material laminated together by adhesives that is described in conjunction with the embodiment shown in FIGS. 1–3, the plates will be compressed under a load of between about 25–70 psi. (about 1,750–4,900 $g/cm^2$). The formed web material is then removed from between the plates. In the embodiment shown in FIGS. 1–3, the formed web material may be provided with between about 40% to about 100% extensibility, and is preferably provided with between about 50% to about 75% extensibility. The available stretch or elongation is increased if for a given number of deformations, the height or degree of deformation imparted to the web material is increased. Similarly, the available stretch or elongation is increased if for a given height or degree of deformation, the number or frequency of deformations is increased. The mating plates can be configured to create any of the patterns for the hinge 54 on the sanitary napkins shown in the drawings.

The sanitary napkin also has zones of extensibility 56 for relieving the stresses that develop in the flaps when they are folded down and under a wearer's undergarment. The terms "zone of extensiblity" or "zone of differential extensibility", as used herein, refer to a portion of the sanitary napkin 20 which is capable of extending (and are preferably capable of extending a greater amount than surrounding portions of the sanitary napkin 20). The sanitary napkin 20 preferably has at least one zone of extensibility 56 for each flap 24, and more preferably has four zones of extensibility 56, one in each quarter of the sanitary napkin 20. Since the zones of differential extensibility 50 relieve stresses in the flaps, they may be referred to herein as a type of "stress relief means".

The zones of extensibility 56 can be extensible in any desired direction, or in more than one direction. However, the zones of extensibility 56 are preferably primarily extensible generally outward in the transverse direction. This is generally in the direction of the arrows shown in FIG. 1. As used herein, "generally in the transverse direction" means that the extensibility has a transverse component. All of the extension, however, need not be exactly parallel to the principal transverse centerline of the sanitary napkin. The extensibility, however, is preferably oriented more in the transverse direction than in the longitudinal direction. The zones of extensibility 56 should be located in the most highly stressed parts of the flaps 24. In the flaps 24 shown in the drawings, the most highly stressed parts of the flaps are regions spaced roughly 45 mm or more from the flap transverse centerline $T_1$, and immediately adjacent regions.

The zones of extensibility 56 can comprise any structure capable of extending in the transverse direction (or in any other direction desired). The extensibility referred to herein, however, should be elasticless. That is, it should be accomplished without the use of separate elastic pieces, strands, or materials to contract one or more portions of the sanitary napkin. The extensibility must also be accomplished without slitting or notching portions of the sanitary napkin that cover the wearer's undergarments. The zones of extensibility 56, therefore, comprise continuous material. This will have the advantage that exudates will not be able to travel through the slits or notches to soil the wearer's undergarments.

Suitable structures for the zones of extensibility 56 include, but are not limited to zones of material that are mechanically strained, corrugated, "ring rolled", formed with a strainable network therein, formed with a network of corrugations without any less extensible bands therein, folded, pleated, or joined along a curved juncture. These structures (although shown only as being part of the flaps 24), can comprise portions of the main body portion 22, portions of the flaps 24, or both. They can be integral parts of these components of the sanitary napkin, or separate elements, such as pieces of material, joined to the sanitary napkin. Suitable structures for the zones of extensibility are described in greater detail in U.S. Pat. No. 5,389,094 issued to Lavash, et al. on Feb. 14, 1995.

Figure 13:
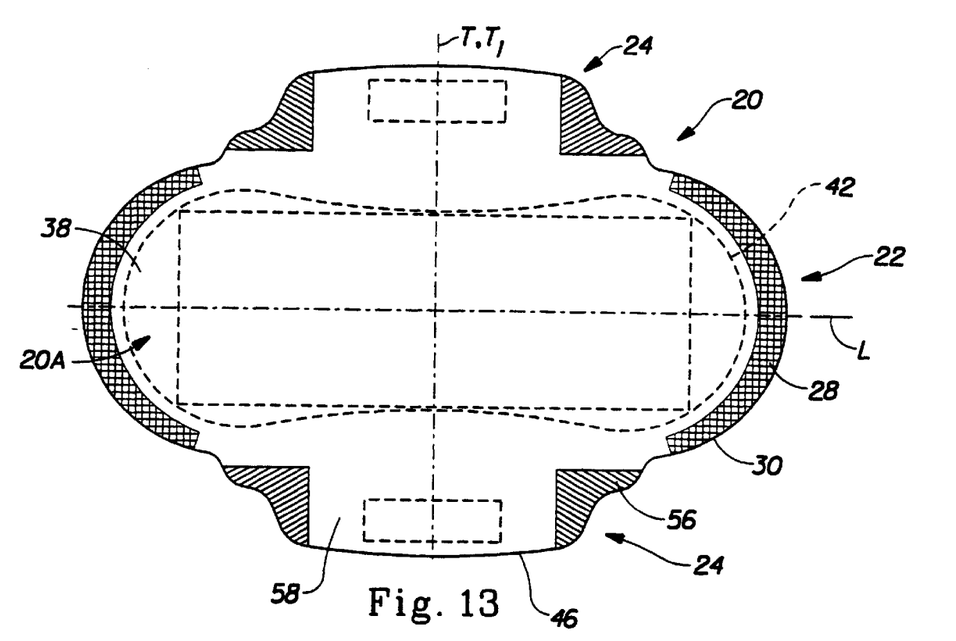
FIG. 13 is another plan view of a sanitary napkin according to the present invention that has an alternative configuration.
Figure 14:
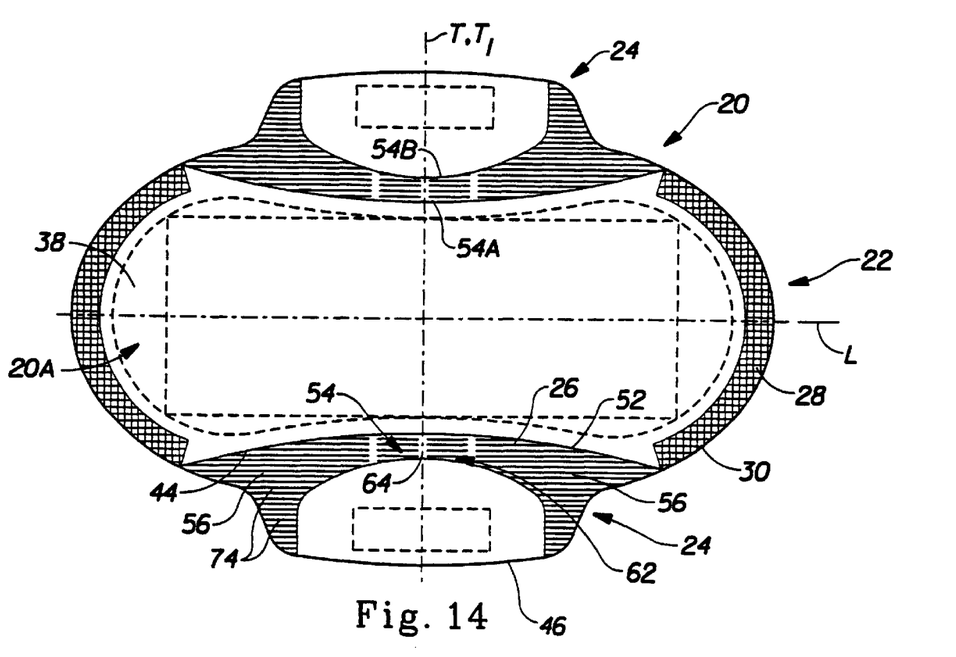
FIG. 14 is another plan view of a sanitary napkin having another alternative configuration.

In the embodiment shown in FIG. 1, the zones of extensibility 56 comprise ring rolled regions of the flaps that preferably have corrugations with ridges that are oriented generally in the longitudinal direction so that the zones of extensibility will be extensible primarily in the transverse direction. In other embodiments, the ridges formed by the ring rolled regions may be oriented at an angle relative to the longitudinal centerline. For example, as shown in FIG. 13, the ring rolled regions may be provided with ridges that form an angle of about 45 degrees with the longitudinal centerline.

There are many possible arrangements and configurations that the zones of extensibility 56 may have relative to each other and relative to the hinges 54. The zones of extensibility 56 (or at least portions thereof) are preferably spaced longitudinally away from the flap transverse centerline $T_1$. As shown in FIG. 1, the portions of the zones of extensibility 56 that are spaced laterally furthest outward from the juncture 52 of the flaps 24 with the main body portion 22 are separated by an intermediate region 58. The portions of the zones of extensibility 56 that are closest to the juncture 52 of the flaps 24 with the main body portion 22 can also be spaced longitudinally away from the flap transverse centerline $T_1$ so that they do not abut each other. Alternatively, these portions of the zones of extensibility 56 can abut each other.

The intermediate region 58 comprises a region of the flaps 24 that includes the flap transverse centerline $T_1$ and laterally adjacent regions. The intermediate region 58 is preferably stiffer than the regions of the sanitary napkin that comprise the hinge 54 and the zones of extensibility 56. This provides the flaps 24 with more integrity so that they will be easier for the user to handle. Thus, the main body portion 22 of the sanitary napkin is preferably the stiffest portion of the sanitary napkin. The intermediate region 58 is preferably the stiffest portion of the flaps 24, and is preferably not as stiff as the main body portion 22. The hinge 54 is preferably more flexible than either of those portions of the sanitary napkin.

The zones of extensibility 56 can be spaced away from the hinge 54, or be adjacent to the hinge 54. Preferably, as shown in FIG. 1, the hinge 54 is contiguous (that is, touching or connected throughout in an unbroken sequence) with the zones of extensibility 56. The hinge 54 and the preferred ring rolled zones of extensibility 56 are, thus, portions of a continuous composite deformed region. As shown in FIG. 1, the hinge 54 gradually transitions into portions of the sanitary napkin that comprise the zones of extensibility 56. The composite deformed region, thus, comprises continuous corrugations having ridges that are generally oriented in the longitudinal direction with a plurality of inextensible bands 64 in the center region adjacent the flap transverse centerline $T_1$.

Figure 12:
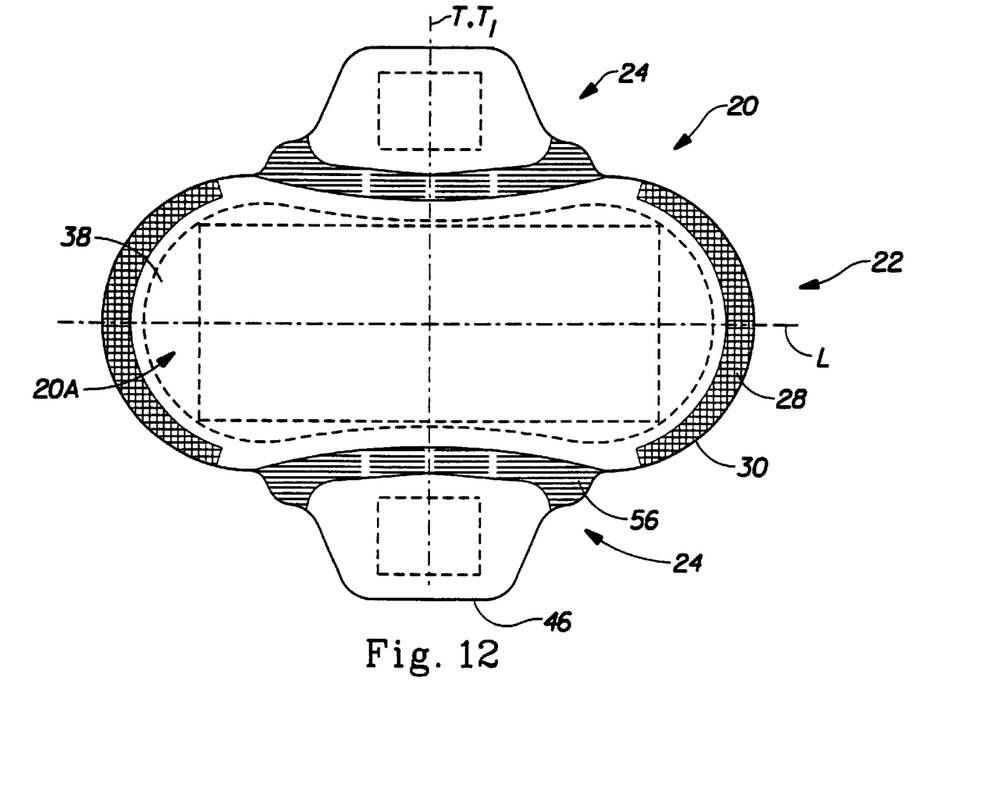
FIG. 12 is another plan view of a sanitary napkin according to the present invention that has an alternative configuration.

The composite deformed region formed by the hinge 54 and the zones of extensibility 56 can be in any suitable configuration. In the embodiment shown in FIG. 1, the composite deformed region preferably has a proximal boundary along the juncture 52 of the flaps 24 with the main body portion 22 that is concave relative to the distal edges 46 of the flaps 24. The composite deformed region preferably has a distal boundary that is roughly in the shape of three sides of a rectangle with rounded corners and a long side that is curvilinear. FIGS. 11–13 show several additional configurations for this region of the sanitary napkin 20. (The embodiment shown in FIG. 13 is not provided with a hinge 54.) In other embodiments, the distal boundary of the composite deformed region that defines the boundary of the intermediate region 58 may be in the form of a generally semi-circular area. In such an embodiment, the radius of curvature of the distal boundary of the composite deformed region can be less than the radius of curvature of the proximal edge of the composite deformed region.

In addition to the configuration of the composite deformed region, many other variations of the embodiments described herein are possible. For example, instead of comprising corrugations with linear ridges that are oriented in the longitudinal direction, the deformations forming these regions can be arranged in the form of a series of concentric concave ridges and valleys that are aligned with the boundaries of these regions. In another example, instead of being a contiguous composite deformed region, the hinge 54 and the zones of extensibility 56 may be separate spaced apart structures. Alternatively, the hinge 54 and/or the zones of extensibility 56, instead of comprising deformed regions of the sanitary napkin, can comprise some other suitable type of structure that provides the sanitary napkin with the desired properties of increased flexibility and extensibility in these regions. The main body portion 22 of the sanitary napkin 20 can also comprise a pair of embossed channels as described in U.S. Pat. No. 5,308,346 issued to Sneller, et al. The features shown and described herein for the various embodiments can also be combined in any other suitable ways to form still more alternative embodiments.

The garment surface 20B of the sanitary napkin 20 may include, and preferably does include, fasteners for attaching the sanitary napkin to the wearer's undergarment. FIG. 1 shows the central pad fastener 80 which is adapted to secure the main body portion 22 of the sanitary napkin to the crotch region of an undergarment. Any types of fasteners known in the art, such as adhesive fasteners and mechanical fasteners can be used. Fasteners comprising adhesives have been found to work well for this purpose, with pressure-sensitive adhesives being preferred. The central pad fastener 80 can be in any suitable configuration, such as a pair of spaced apart longitudinally-oriented strips or zones of adhesive that are centered about the longitudinal centerline L, or as shown in FIG. 1, a single zone of adhesive 80 that is centered about the longitudinal centerline L.

The outer surface of the flaps 24, adjacent the distal edges 46 of the flaps, is preferably provided with a flap fastener, such as flap adhesive 82. The flap adhesive 82 is used to assist in maintaining the flaps 24 in position after they are wrapped around the edge of the crotch portion of the panty. While the flap adhesive 82 can be of any suitable size, it is preferably between about 60% and about 80% of the length of the distal portion 24B of the flaps 24. Suitable adhesive fasteners are described in greater detail in U.S. Pat. No. 4,917,697. The flaps 24 can be maintained in position by attaching the flaps 24 to the undergarment, or to the opposing flap.

The fasteners, central pad fastener 80 and flap fasteners 82, used with the present invention are not limited to adhesive attachment means. Any type of fastener used in the art can be used for such purpose. For example, the sanitary napkin 20 could be secured to the wearer's undergarment by mechanical fasteners, such as VELCRO hook material, or the fasteners described in U.S. Pat. No. 4,946,527 entitled "Pressure-Sensitive Adhesive Fastener and Method of Making the Same" issued to Battrell on Aug. 7, 1990, or U.S. Pat. 5,392,498 entitled "Non-Abrasive Skin Friendly Mechanical Fastening System" issued to Goulait, et al. on Feb. 28, 1995. For simplicity, however, the fasteners will be described in terms of adhesive attachment means.

The adhesive attachment means are respectively covered by removable release liners, central pad release liner and flap release liner, both designated 84. The pressure-sensitive adhesives should be covered with release liners 84 to keep the adhesives from sticking to extraneous surfaces prior to use. Suitable release liners are described in U.S. Pat. 4,917, 697. In a preferred embodiment, the flaps 24 are folded over the topsheet and the flap adhesives 82 are covered by a single release paper. The adhesvie attachment means on such flaps could, instead of being covered with a release liner, be releasably adhered to a release surface provided on some other portion of the sanitary napkin, including the main body portion, or the flaps, or a separate component attached to the main body portion or the flaps. For example, the flaps 24 could be folded and tucked as described in U.S. Pat. No. 5,281,209 issued to Osbom, et al. on Jan. 25, 1994. The sanitary napkin 20 may additionally be provided with a particularly preferred release liner which also serves as an individual package for wrapping the sanitary napkin is described in U.S. Pat. No. 4,556,146 issued to Swanson, et al.

Figure 4:
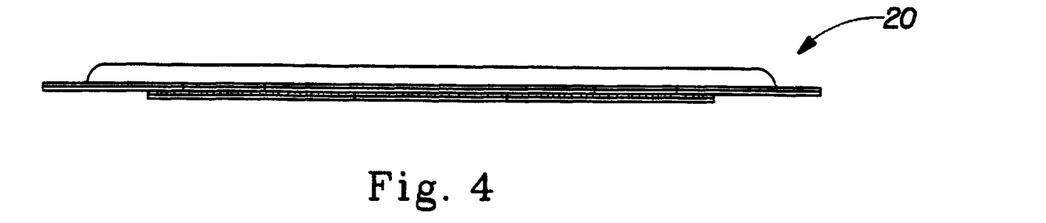
FIG. 4 is a simplified side view of the sanitary napkin shown in FIGS. 1–3.
Figure 5:
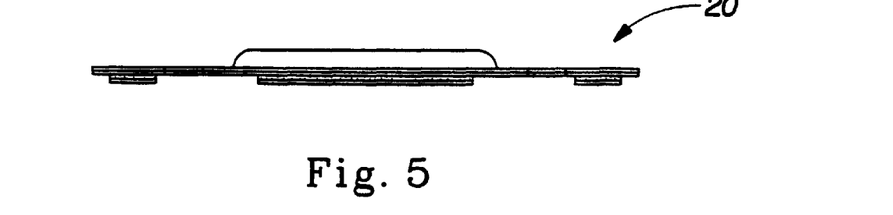
FIG. 5 is a simplified end view of the sanitary napkin shown in FIGS. 1–3.
Figure 6:
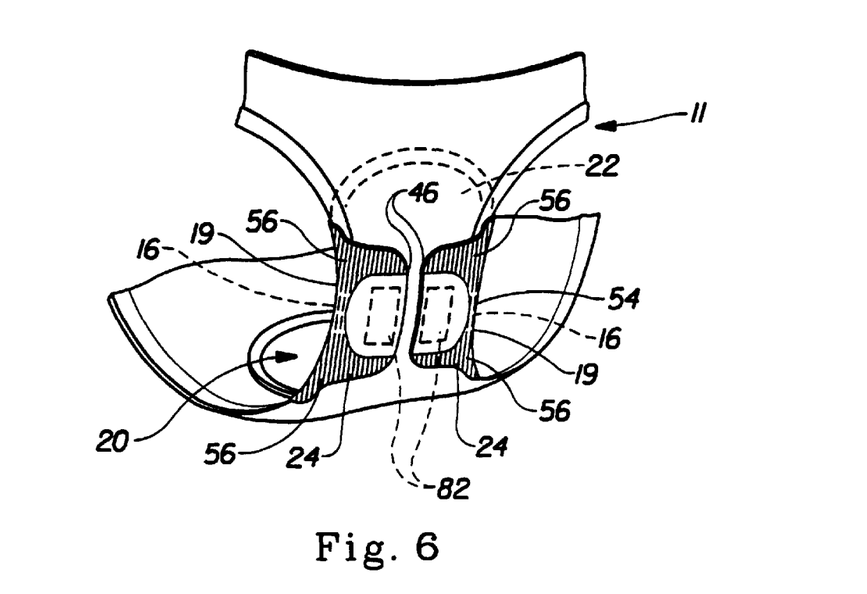
FIG. 6 is a pespective view of the crotch portion of a woman's panties with the sanitary napkin shown in FIGS. 1–3 in place therein.

The sanitary napkin 20 of the present invention is utilized by removing the release liners 84 and placing the sanitary napkin 20 in a panty 11 as shown in FIG. 4. The main body portion 22 is placed in the crotch portion of the panty with one end of the main body portion 22 extending towards the front section of the panty and the other end towards the back section of the panty. The backsheet 40 is placed in contact with the inner surface of the center of the crotch portion of the panty. The central pad adhesive fastener 80 maintains main body portion 22 in position. The flaps 24 are then folded around the side edges 16 of the panty. The flap adhesives 82 secure the flaps 24 to the underside of the panty or to the opposing flap.

Other embodiments of the absorbent articles described herein are also possible. For example, in alternative embodiments, instead of being provided with flaps, the absorbent article could be provided with undergarment covering components or ("side wrapping elements") that have a smaller span than conventionally sized flaps and that do not have to be manipulated by the wearer when placed in the wearer's undergarments. Absorbent articles having side wrapping elements are described in allowed U.S. patent application Ser. No. 08/096,121 entitled "Absorbent Articles Having Panty Covering Components That Naturally Wrap the Sides of Panties" filed Jul. 22, 1993, in the name of Lavash, et al. (PCT Publication No. WO 94/02096, published Feb. 3, 1994); U.S. patent application Ser. No. 08/124, 180 entitled "Absorbent Articles Having Panty Covering Components Comprising Extensible Web Materials Which Exhibit Elastic-Like Behavior" filed Sep. 17, 1993, in the name of Mansfield, et al. (PCT Publication No. WO 95/07675, published Mar. 23, 1995); and U.S. Pat. No. 5,558,663 entitled "Absorbent Articles Having Undergarment Covering Components With Zones of Extensibility" issued to Weinberger, et al. on Sep. 24, 1996.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention.

List of Elements

Reference letters

| | |
|---|---|
| A | angle of edge of flaps |
| E | panty elastics |
| L | longitudinal centerline |
| S | step in the flap |
| T | transverse centerline |
| T1 | flap transverse centerline |

Reference numbers

| | |
|---|---|
| 11 | panty |
| 16 | side edges of the panty |
| 19 | fold in the flap along edge of the panty |
| 20 | sanitary napkin |
| 20A | body surface of sanitary napkin |
| 20B | garment surface of sanitary napkin |
| 22 | main body portion of sanitary napkin |
| 24 | flaps |
| 24A | proximal portions of flaps |
| 24B | distal portions of flaps |
| 24C | additional material in proximal portions of flaps |
| 26 | longitudinal side edges of main body portion of sanitary napkin |
| 28 | end edges of main body portion |
| 30 | periphery of main body portion |
| 32 | end region of sanitary napkin |
| 34 | end region of sanitary napkin |
| 36 | central region of sanitary napkin |
| 38 | topsheet |
| 40 | backsheet |
| 42 | absorbent core |
| 44 | proximal edge of flaps |
| 46 | distal edge of flaps |
| 47 | outer edge or periphery of the flaps |
| 48 | front half of flaps |
| 50 | back half of flaps |
| 52 | juncture of flaps with main body portion |
| 54 | hinge |
| 54A | inwardmost boundary of the hinge (proximal edge) |
| 54B | outer boundary of the hinge (distal edge) |
| 56 | zones of extensibility |
| 58 | stiffened intermediate region between zones of extensibility |
| 59 | fold lines in the ring rolling corrugations |

-continued

| | List of Elements |
|---|---|
| 60 | web material having strainable network formed therein |
| 62 | strainable network |
| 64 | first region of strainable network |
| 66 | second region of strainable network |
| 68 | first axis of first region |
| 69 | second axis of first region |
| 70 | first axis of second region |
| 71 | second axis of second region |
| 72 | |
| 74 | deformations |
| 76 | first axis of deformations |
| 77 | second axis of deformations |
| 78 | |
| 80 | central pad adhesive |
| 82 | flap adhesive |
| 84 | adhesive cover strips |
| 86 | |
| 88 | |
| 90 | |
| 92 | |
| 94 | |
| 96 | |
| 98 | |
| 100 | |

What is claimed is:

1. An absorbent article having a liquid pervious body-facing side, a liquid impervious garment side, a principal longitudinal centerline extending in a longitudinal direction, and a principal transverse centerline extending in a transverse direction, said absorbent article comprising:

a main body portion having a central region, two spaced apart longitudinal side edges and two spaced apart end edges, said main body portion comprising an absorbent core positioned between said body-facing side and said garment side; and a pair of flaps joined to said main body portion at a juncture, each flap extending laterally outward beyond one of the longitudinal side edges of said main body portion in at least the central region of said main body portion to a distal edge, said flaps each having a flap transverse centerline that passes through said central region of said main body portion, said flaps comprising a proximal portion adjacent to said juncture and a distal portion located adjacent to the distal edge of said flaps, said flaps having a step configuration in which a portion of the flaps adjacent to the juncture is longer as measured in the longitudinal direction than a portion of the flaps located adjacent to the distal edges of the flaps and there is a discontinuity in the outer edge of the flaps between said proximal portion and said distal portion, and the length of the distal portions of the flaps as measured in the longitudinal direction is between about 50% and about 80% of the length of the proximal portions of said flaps, wherein said flaps comprise portions of said topsheet and said backsheet that extend laterally outward beyond the longitudinal side edges of said absorbent core from at least said central region of said main body portion, and said portions are partially peripherally joined together by adhesives, and are partially unbonded to leave an adhesive-free window at the interface between said portions of said topsheet and said backsheet that form said flaps.

* * * * *